(12) United States Patent
Moore, Jr.

(10) Patent No.: US 11,071,618 B2
(45) Date of Patent: Jul. 27, 2021

(54) LYMPH NODE REPLACEMENT CONSTRUCT

(71) Applicant: James E. Moore, Jr., London (GB)

(72) Inventor: James E. Moore, Jr., London (GB)

(73) Assignee: James Edward Moore, Jr., London (GB)

( * ) Notice: Subject to any disclaimer, the term of this patent is extended or adjusted under 35 U.S.C. 154(b) by 0 days.

(21) Appl. No.: 15/528,936

(22) PCT Filed: Nov. 23, 2015

(86) PCT No.: PCT/GB2015/053560
§ 371 (c)(1),
(2) Date: May 23, 2017

(87) PCT Pub. No.: WO2016/083784
PCT Pub. Date: Jun. 2, 2016

(65) Prior Publication Data
US 2017/0340430 A1    Nov. 30, 2017

(30) Foreign Application Priority Data

Nov. 24, 2014    (GB) ...................................... 1420829

(51) Int. Cl.
*A61F 2/02*        (2006.01)
*B33Y 10/00*       (2015.01)
(Continued)

(52) U.S. Cl.
CPC .............. *A61F 2/022* (2013.01); *B33Y 10/00* (2014.12); *B33Y 80/00* (2014.12);
(Continued)

(58) Field of Classification Search
CPC .......... A61F 2/02; B29C 64/00; A61M 5/142; A61B 5/00
See application file for complete search history.

(56) References Cited

U.S. PATENT DOCUMENTS

| | | | |
|---|---|---|---|
| 4,657,530 A | 4/1987 | Buchwald et al. | |
| 8,430,832 B2 * | 4/2013 | Humes | A61P 13/12 604/6.03 |

(Continued)

FOREIGN PATENT DOCUMENTS

| | | |
|---|---|---|
| CN | 103002832 A | 3/2013 |
| GB | 1479002 | 7/1977 |

(Continued)

OTHER PUBLICATIONS

"Tissue-engineered lymphatic graft for the treatment of lymphedema" Journal of Surgical Research 2014, Kanapathy et. al. 2014.

*Primary Examiner* — Yashita Sharma
(74) *Attorney, Agent, or Firm* — Snell & Wilmer L.L.P.

(57) ABSTRACT

An implantable lymph node replacement construct (10) comprising a body (12) having a plurality of inlets (24,26) and a lesser number of outlets (30). The body (12) further having an internal structure defining a fluid communication path through the body (12) from the inlets (24,26) to the outlet or outlets (30). The internal structure of the body (12) comprises an inlet portion (38), a convergent portion (40) and an outlet portion (42) such that lymph received by the construct (10) at the inlets (24,26) is conveyed through the inlet portion (38) of the internal structure to the convergent portion (40) whereupon the lymph is combined before passing to the outlet or outlets (30).

20 Claims, 16 Drawing Sheets

(51) Int. Cl.
  *B33Y 80/00*   (2015.01)
  *B29L 31/00*   (2006.01)
  *A61M 5/14*    (2006.01)
  *A61M 5/142*   (2006.01)

(52) U.S. Cl.
  CPC .......... *A61F 2240/002* (2013.01); *A61M 5/14* (2013.01); *A61M 5/142* (2013.01); *B29L 2031/7532* (2013.01)

(56) References Cited

U.S. PATENT DOCUMENTS

| | | |
|---|---|---|
| 10,369,263 B2 * | 8/2019 | Labib .................... B01D 69/084 |
| 2002/0173842 A1 | 11/2002 | Buchanan |
| 2005/0101882 A1 * | 5/2005 | Leira .................... A61B 5/14514 600/579 |
| 2005/0103340 A1 | 5/2005 | Wondka |
| 2006/0171988 A1 | 8/2006 | Hilf |
| 2007/0050013 A1 * | 3/2007 | Gross .................... A61F 2/2412 623/1.24 |
| 2007/0119781 A1 * | 5/2007 | Huang .................. B01D 63/021 210/645 |
| 2008/0267924 A1 * | 10/2008 | Alitalo .................... A61P 7/10 424/93.7 |

FOREIGN PATENT DOCUMENTS

| | | |
|---|---|---|
| JP | 2004255110 | 9/2004 |
| JP | 2006129839 | 5/2006 |
| JP | 2012036151 | 2/2012 |
| WO | 9938453 | 8/1999 |
| WO | 2014015377 | 1/2014 |

* cited by examiner

LYMPH NODE REPLACEMENT CONSTRUCT

RELATED APPLICATIONS

This application is a 371 U.S. National Stage Application of International Application No. PCT/GB2015/053560, entitled "LYMPH NODE REPLACEMENT CONSTRUCT," and filed on Nov. 23, 2015, which claims priority from GB Patent App. No. 1420829.2, filed on Nov. 24, 2014, the entire contents of which are incorporated herein by reference as if set forth in full.

FIELD OF THE INVENTION

The present invention relates to an implantable lymph node replacement construct.

BACKGROUND

The removal of lymph nodes is commonly part of cancer surgery procedures as a means of minimizing the risk of metastatic spread of tumour cells. Many of the patients that undergo lymph node removal eventually develop edema due to a reduction in fluid drainage from surrounding tissues caused by disruption of the local lymphatic system. For breast cancer patients who undergo mastectomy, removal of lymph nodes under the arm can lead to edema in the arm. Edema of this type is a painful, debilitating condition that has no cure. Current treatment strategies include massage, static compression wrapping and dynamic compression using pneumatic cuffs.

Artificial lymph nodes are described in JP 2004255110A, JP2012036151A, US2006171988A and JP2006129839A. The nodes described in these references are formed from collagen sponge materials and thus only partially recreate the form of an actual lymph node. These references describe embedding sponge-like structures with immune cells. They do not address the need to restore the flow pathways that have been interrupted by lymph node resection. Issues surrounding the use of biodegradable synthetic, nonbiodegradable synthetic and natural (decellularized) scaffold based solutions are discussed in an article entitled "Tissue-engineered lymphatic graft for the treatment of lymphedema" (Journal of Surgical Research 2014, Kanapathy et. al.).

SUMMARY OF THE INVENTION

According to a first aspect of the present invention there is provided an implantable lymph node replacement construct comprising:
 a body having one or more inlets and one or more outlets;
 the body further having an internal structure defining one or more fluid communication paths through the body, from the inlet or inlets, to the outlet or outlets;
 the internal structure being enclosed within the body, which surrounds the internal structure, wherein the internal structure of the body comprises a plurality of parallel flow paths extending through and within at least a part of the body, the internal structure configured such that lymph received by the body at the inlet or inlets is conveyed through the parallel flow paths within the body, before passing to the outlet or outlets.

Parallel flow paths need not be parallel in geometric terms, but represent parallel flow flowing through the body of the device in a generally neighbouring fashion, co-extending from an inlet end to an outlet end of the construct, as distinct from series flow paths connected in series with one another.

The plural parallel flow paths may be enclosed or encapsulated within a common enclosure defined by the body.

The body may comprise an outer surface extending around the plural parallel flow paths, so that the flow paths are laterally contained within the outer surface.

A further aspect of the invention provides an implantable lymph node replacement construct comprising a body having a plurality of inlets and a lesser number of outlets, the body further having an internal structure defining a fluid communication path through the body from the inlets to the outlet or outlets, wherein the internal structure of the body comprises an inlet portion, a convergent portion and an outlet portion such that lymph received by the body at the inlets is conveyed through the inlet portion of the internal structure to the convergent portion whereupon the lymph is combined before passing to the outlet or outlets.

The present invention can thus provide a surgically implantable construct that is able to function in a similar manner to a lymph node by receiving, and preferably combining, lymph from afferent lymph vessels connected to or adjacent the inlets, and delivering the preferably combined lymph to one or more efferent lymph vessels connected to or adjacent the outlet or outlets. The plurality of inlets seeks to conform to the typical terminal configuration of an afferent lymph vessel, as such afferent lymph vessels divide into multiple vessels before approaching a lymph node.

By providing the construct with a plurality of inlets, parallel flow paths and/or outlets, the construct presents reduced resistance to the entry of lymph flow into, out of, and/or through the construct compared to a construct having a single inlet, outlet or single flow path. As will readily be understood by the skilled addressee, the flow resistance presented to the afferent lymph vessels is inversely proportional to the number of flow paths, represented by inlets, internal fluid communication paths of the construct, or outlets, where they generally have substantially the same diameter of individual flow resistance per conduit. The construct is also able to receive lymph flow from multiple sources and deliver said flows concurrently to a lesser number of outlets.

The inlet portion of the internal structure of the body may include a corresponding plurality of inlet conduits extending from the plurality of inlets to the convergent portion of the internal structure.

By providing the construct with a corresponding plurality of inlet conduits, the construct presents reduced resistance to lymph flow through the construct compared to a construct with a single inlet conduit. As noted above in relation to the multiple inlets, the provision of corresponding plurality of inlet conduits presents a flow resistance that is inversely proportional to the number inlet conduits. The inlet conduits may each be of approximately equal length.

The convergent portion of the internal structure of the body may comprise a manifold extending from the inlet conduits to the outlet portion of the internal structure of the body. The manifold enables lymph flow from the inlet conduits to be combined in a controlled manner.

The outlet portion of the internal structure of the body may comprise outlet conduits extending from the manifold to the or each outlet of the body. The or each outlet conduit provides a clearly defined route for the combined lymph flow to move through the construct from the manifold to the construct outlet or outlets. The or each outlet conduit may have a diameter that is approximately equal to the diameter of the or each inlet conduit. In an alternative embodiment, the outlet conduit may have a diameter that is different to that of the or each inlet conduit. Differing inlet and outlet conduit diameters may be utilised in order to, for example, maintain a constant shear stress in the lymph passing through the construct. This may help to discourage pathogenic behaviour in the endothelial cells that eventually may line the inner surface of the internal structure of the construct.

According to a second aspect of the present invention there is provided an implantable lymph node replacement construct comprising a body having a one or more inlets and a greater number of outlets, the body further having an internal structure defining a fluid communication path through the body from the inlet or inlets to the outlets, wherein the internal structure of the body comprises an inlet portion, a divergent portion and an outlet portion such that lymph received by the body at the inlet or inlets is conveyed through the inlet portion of the internal structure to the divergent portion whereupon the lymph flow is split before passing to the outlets.

According to a third aspect of the present invention there is provided an implantable lymph node replacement construct comprising a body having a plurality of inlets and an equal number of outlets, the body further having an internal structure defining a fluid communication path through the body from the inlets to the outlets, wherein the internal structure of the body comprises a plurality of separate conduits each extending through the body from an inlet to a corresponding outlet.

In certain embodiments, the fluid communication path through the body includes one or more fluid retention spaces where lymph can reside for a longer period in use. Such spaces may be used to encourage exposure of the lymph to biological macromolecules and cells disposed within those spaces. This could provide replacement of at least some of the immunological function of the removed lymph node. The one or more fluid retention spaces may, for example, be realised by the provision of a porous medium, where the porosity may be homogeneous or inhomogeneous. In the latter case, more porous structures may be provided around the periphery of the space to minimise flow resistance.

The internal structure of the body may include a unidirectional valve arranged to prevent the backflow of lymph in the direction from the or each outlet to the inlet or inlets. In one embodiment, one or more of inlet conduits may include a unidirectional valve arranged to prevent the backflow of lymph in the direction from the or each outlet to one or more of the inlets. Furthermore, the or each outlet conduit may include a unidirectional valve arranged to prevent the backflow of lymph in the direction from the outlet to the inlets.

The presence of one or more unidirectional valves within the construct enables the construct to function in a manner more closely akin to lymphatic vessels. The or each valve may open and close in response to fluid pressure within the construct. Additionally, the or each valve may be caused to open and close by external manipulation of the construct. The construct may comprise first and second uni-directional valves, the first unidirectional valve arranged between the inlet or outlet and the second unidirectional valve, such that external manipulation of the construct can open the valves to assist in the movement of lymph in the construct.

The implantable lymph node replacement construct may therefore be configured such that external manipulation of the construct can be used to pump lymph through the device via the unidirectional valves.

The or each unidirectional valve may be either a monoleaflet type valve or a bi-leaflet type valve. In an alternative embodiment, the or each unidirectional valve may have no moving parts, where the unidirectional function is realised through the use of baffles, projections, recess and such like within the internal structure of the construct.

The construct is fabricated from a biocompatible material.

In one embodiment, the construct may be fabricated from a compliant, resilient material such as, for example, a polymer, and more specifically a hydrogel polymer. Such a material allows the shape of the construct to be changed by the application of external pressure. Such pressure may be applied to the construct by normal movement of the surrounding tissues and body structures. Alternatively, or additionally, pressure may be applied to the construct by massage, squeezing or like manipulation by either the person within whom the construct is implanted or another person. The application of pressure to the construct in the manners described above will assist in the movement of lymph through the construct following implantation. As will be readily appreciated by the skilled person, such manipulation of the construct to assist the flow of lymph therethrough would work particularly well when the aforementioned unidirectional valves are present within the construct.

Suitable polymers from which the construct may be fabricated include polypropylene, polygylcolic acid, polycaprilactone and poly L lactic acid.

In an alternative embodiment, the construct may be fabricated from rigid biocompatible material such as, for example, a metal or a ceramic.

The construct may be provided with one or more biologically active substances, preferably disposed within the internal structure of the body. Suitable active substances include growth factors (such as vascular endothelial growth factor C or VEGF-C etc.), or other substances that encourage lymphatic vessel connection and ingrowth. Substances of this type may suitably be disposed internally of the construct, for example upon surfaces thereof, and preferably towards the inlet and/or outlet portions. Alternatively, such substances may be embedded within the material from which the construct is fabricated. In yet an alternative embodiment, the biologically active substances may be suspended or otherwise retained within another material and then injected or otherwise introduced into interstices of the construct.

Other active substances include inhibitors of thrombus formation, such as heparins. Again these substances are preferably disposed internally of the construct. Alternatively or additionally, the construct may be provided, internally or externally, with one or more substances which can attenuate the implant recipient's immunological response to the implanted construct, so as to minimise inflammatory reactions at the implant site and avoid rejection of the implanted construct. Such substances are well known to the skilled person, but may include hydrophilic coating materials (such as PEG), or inhibitors of inflammatory mediators.

Two or more implantable lymph node replacement constructs according to the invention may be connected or otherwise joined together to form an implantable assembly.

According to a further aspect of the present invention there is provided a method of manufacturing a lymph node replacement construct according to the first aspect comprising the steps of:

providing a computer-readable medium having computer executable instructions adapted to cause a 3-D printer to print a lymph node replacement construct comprising a body having first and second inlets and an outlet, the body further having an internal structure defining a fluid communication path through the body from the inlets to the outlet, wherein the internal structure of the body comprises an inlet portion, a convergent portion and an outlet portion such that lymph received by the body at each inlet is conveyed through the inlet portion of the internal structure to the convergent portion whereupon the lymph is combined before passing to the outlet; and printing the lymph node replacement construct.

It will be appreciated that 3D printing may be utilised to fabricate lymph node replacement constructs have alternative configurations such as, for example, a greater number of outlets than inlets, and an equal number of outlets to inlets. Similarly, the printed construct may have an alternative internal structure including, for example, a divergent portion or individual conduits extending between respective inlets and outlets.

It will further be appreciated that other methods of fabricating the construct are possible including, but not limited to, electrostatic or biological self-assembly, electrospinning and mechanical machining.

According to another aspect of the present invention there is provided a computer-readable medium having computer executable instructions adapted to cause a 3-D printer to print a lymph node replacement construct comprising a body having first and second inlets and an outlet, the body further having an internal structure defining a fluid communication path through the body from the inlets to the outlet, wherein the internal structure of the body comprises an inlet portion, a convergent portion and an outlet portion such that lymph received by the body at each inlet is conveyed through the inlet portion of the internal structure to the convergent portion whereupon the lymph is combined before passing to the outlet.

As above, the computer executable instructions may be written so as cause a 3-D printer to print lymph node replacement constructs have alternative configurations such as, for example, a greater number of outlets than inlets, and an equal number of outlets to inlets. Similarly, the printed construct may have an alternative internal structure including, for example, a divergent portion or individual conduits extending between respective inlets and outlets.

According to a further aspect of the present invention there is provided a method of implanting a lymph node replacement construct according to the first aspect comprising the steps of:

providing the lymph node replacement construct; and implanting the lymph node replacement construct into the lymphoid drainage system of a subject requiring such an implant, for example following lymph node removal surgery.

The subject is preferably a human.

BRIEF DESCRIPTION OF THE DRAWINGS

Embodiments of the present invention will now be described with reference to the accompanying drawings in which.

DESCRIPTION OF VARIOUS EMBODIMENTS

Figure 1:
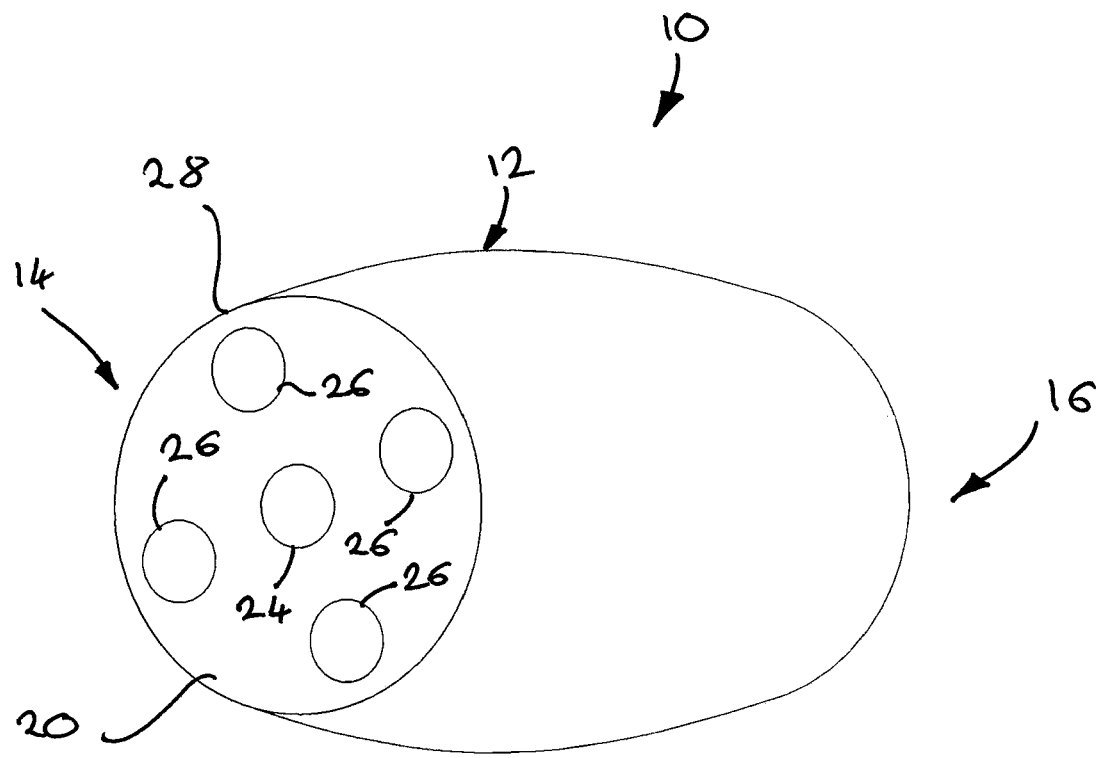
FIG. 1 shows a perspective view of a lymph node replacement construct according to a first embodiment of the present invention.
Figure 2:
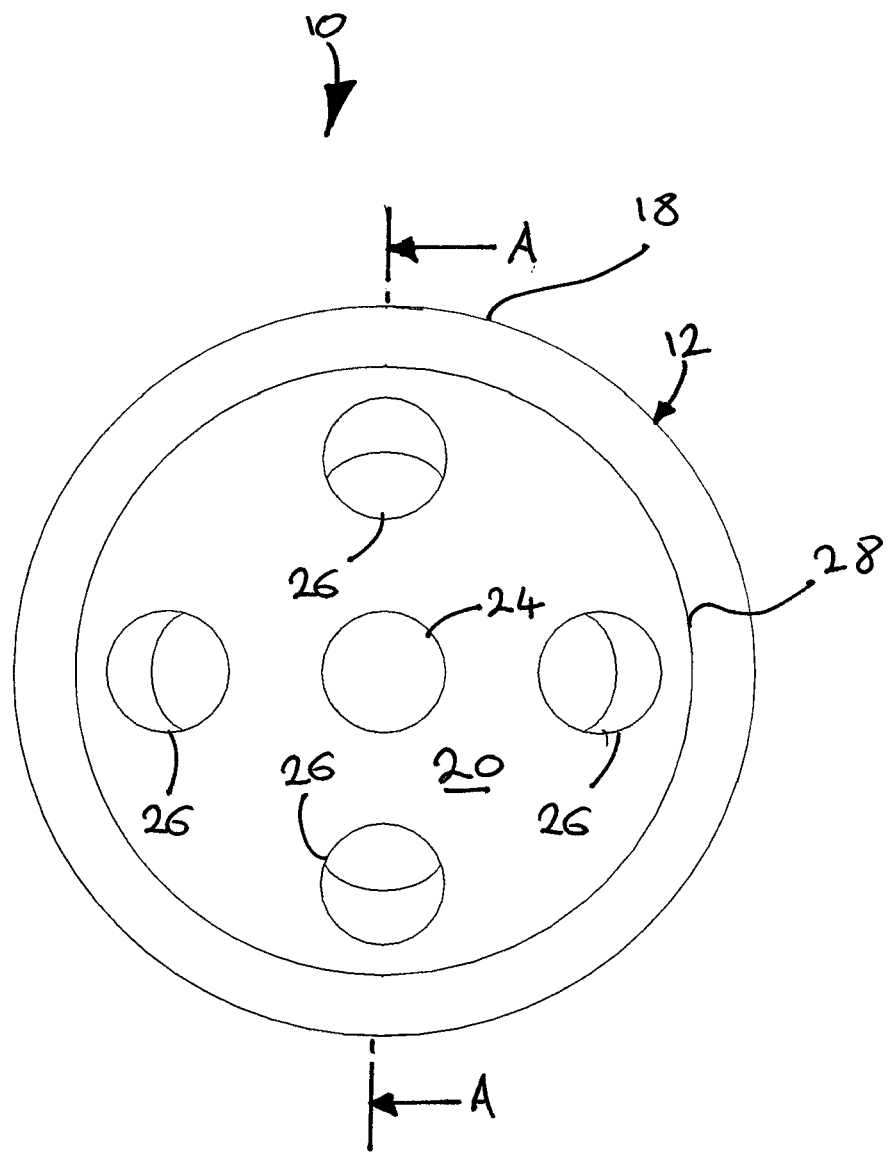
FIG. 2 shows an end view of the inlet end of the construct of FIG. 1.
Figure 3:
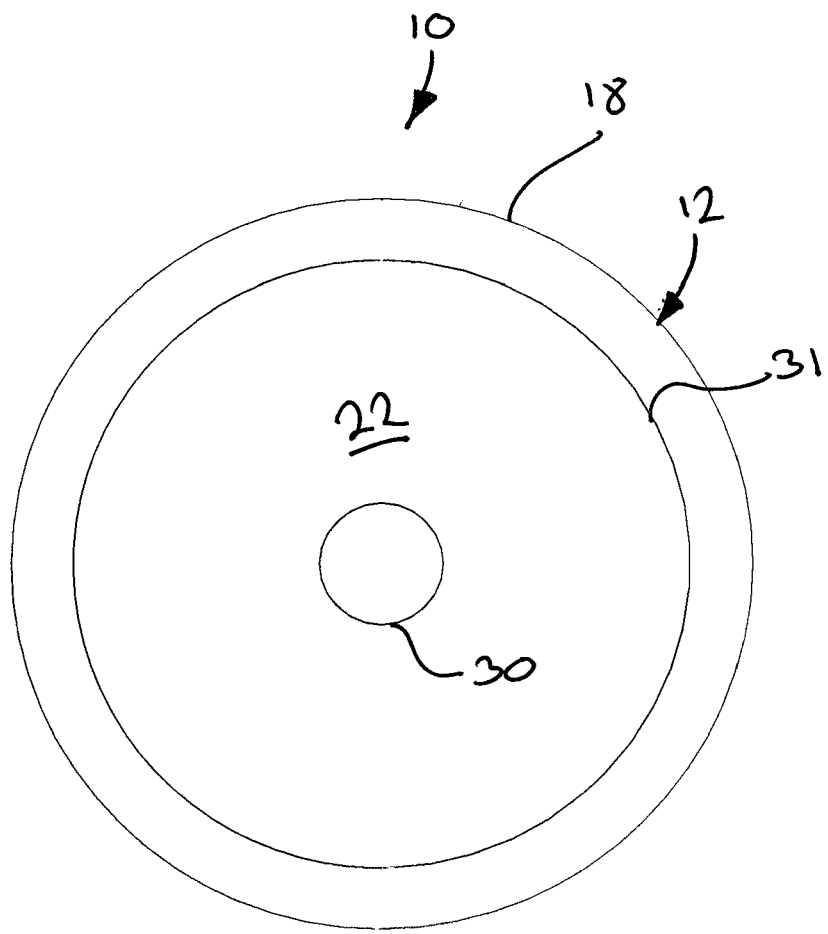
FIG. 3 shows an end view of the outlet end of the construct of FIG. 1.
Figure 4:
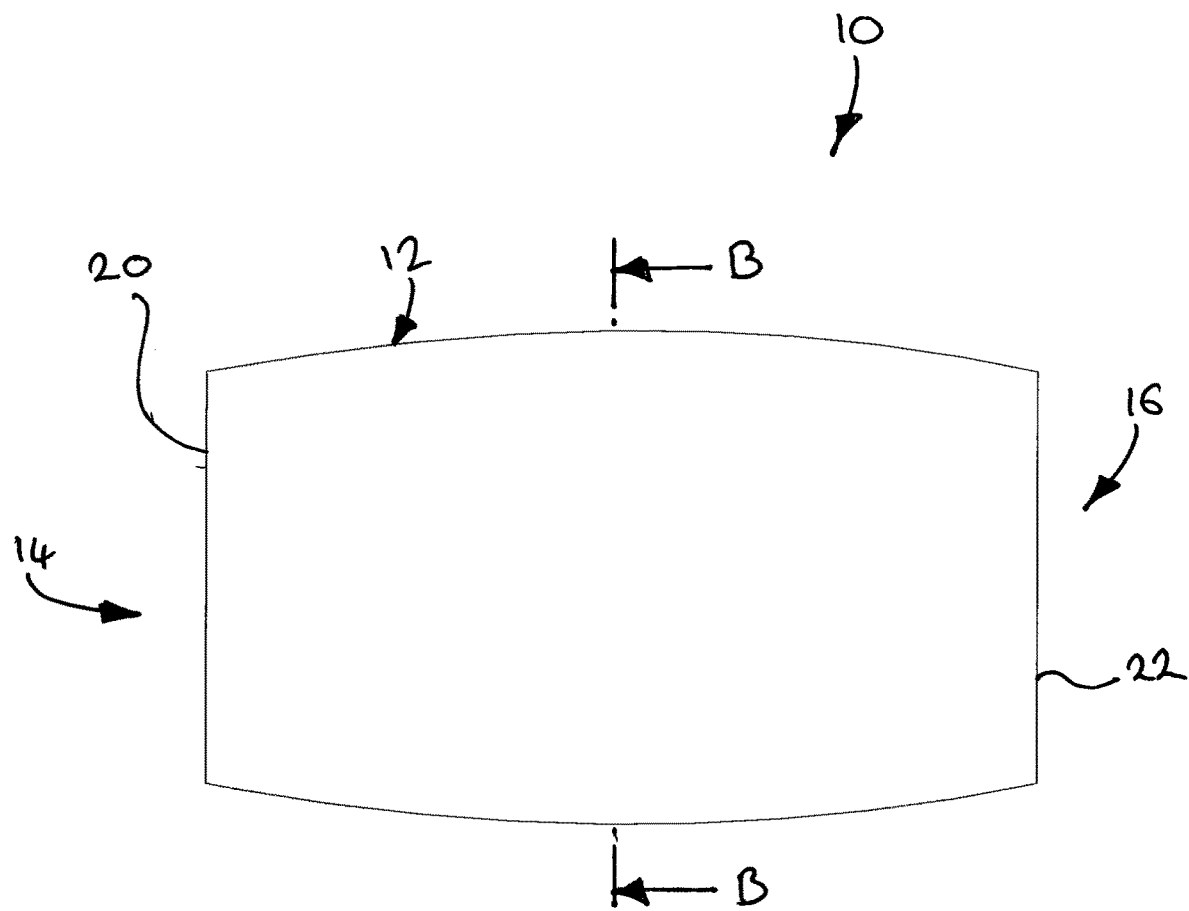
FIG. 4 shows a side view of the construct of FIG. 1.

Referring firstly to FIGS. 1 to 6 there is shown a first embodiment of a lymph node replacement construct generally designated 10. The construct 10 comprises a body 12 having, and as will be described in greater detail below, an arrangement of conduits extending therethrough. In the embodiment shown, the body 12 is substantially cylindrical and has a "barrel" shaped appearance whereupon the diameter of the body 12 at each end 14,16 is less than the diameter of the body 12 at substantially its mid-section 18. As can be readily appreciated from the Figures, plural parallel flow paths are encapsulated within a common enclosure defined by the body 12. That is to say, the flow paths all extend within the body and are surrounded by an outer surface of the body. In particular, parallel flow paths extend within the enclosure and any areas between the parallel flow paths are contained with the enclosure defined by the body and its outer surface.

A flat circular end-face 20,22 is provided at each end 14,16 of the body 12. In the embodiment shown the planes upon which the end-faces lie are substantially parallel, although such parallel relation between the end faces 20,22 is not essential. The end faces 20,22 of the body 12 comprise, respectively, an inlet end face 20 and an outlet end face 22 of the construct 10.

The inlet end-face 20 is provided with five circular inlet apertures comprising a single central inlet aperture 24 and four satellite inlet apertures 26 which are spaced, in the embodiment shown, equidistantly around the central inlet aperture 24. The satellite inlet apertures 26 are arranged on a pitch circle that is greater than the diameter of the central inlet aperture and less that the diameter of the inlet end-face 20. The pitch circle and inlet aperture 24, 26 diameters are such that the inlet apertures 24,26 are provided fully within the boundary described by the edge 28 of the inlet end face 20. In the embodiment shown, the inlet apertures 24,26 are all of approximately equal diameter.

The outlet end face 22 is provided with a single, centrally positioned outlet aperture 30. In the embodiment shown, the outlet aperture 30 has a diameter that is approximately equal to the diameter of each of the inlet apertures 24,26 and, as such the outlet aperture 30 is provided fully within the boundary described by the edge 31 of the inlet end face 20. In an alternative embodiment, the outlet aperture 30 may have a diameter that is greater than that of the inlet apertures 24,26. Differing inlet and outlet aperture diameters may be utilised in order to maintain a constant shear stress in the lymph passing through the construct 10. This may help to discourage pathogenic behaviour in the endothelial cells that eventually may line the inner surface of the internal structure of the construct 10.

Figure 5:
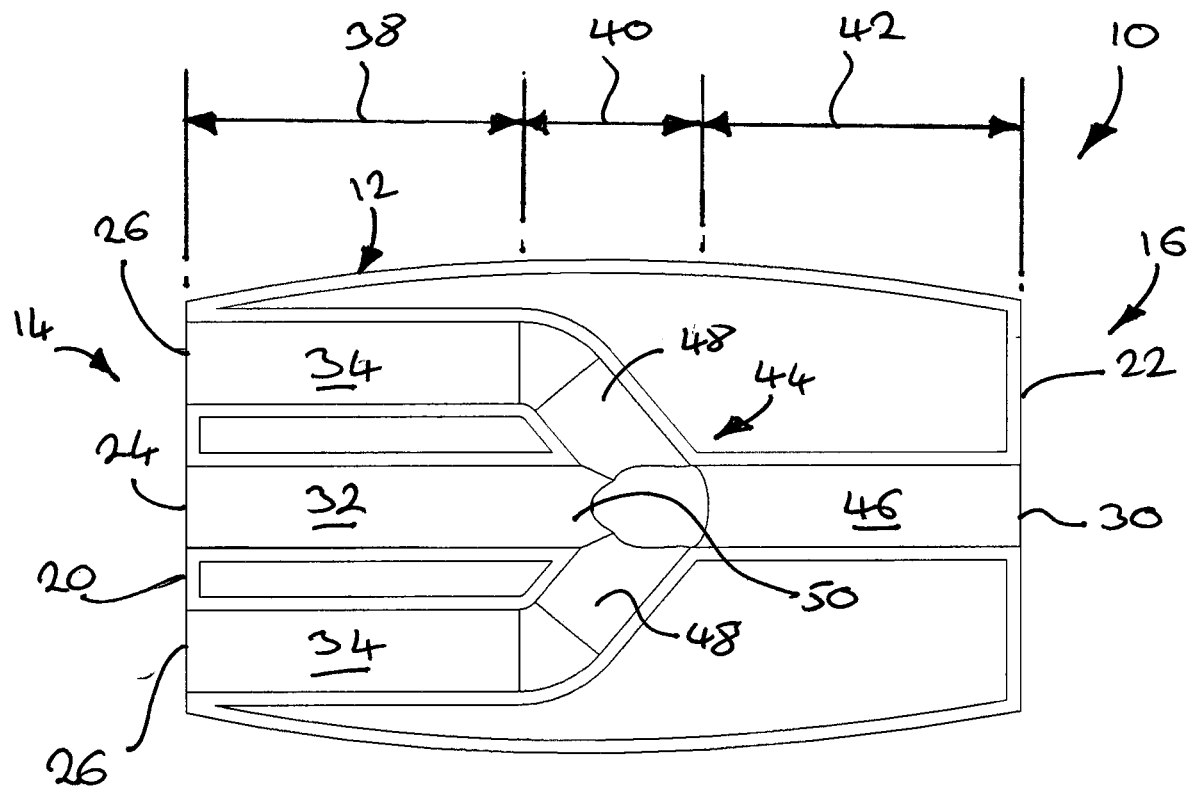
FIG. 5 shows the longitudinal cross-sectional view of the construct as indicated by line A-A of FIG. 2.
Figure 6:
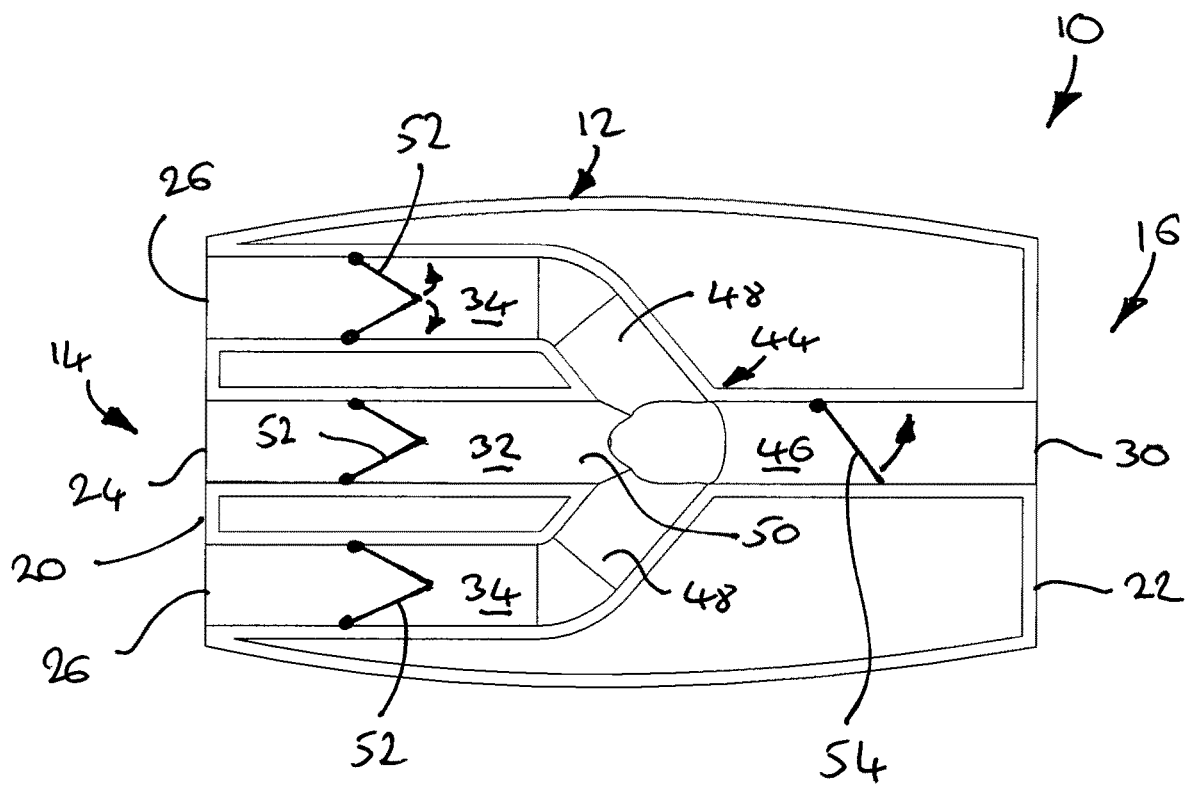
FIG. 6 shows the above referenced longitudinal cross-sectional view of the construct including internal valve structures.
Figure 7:
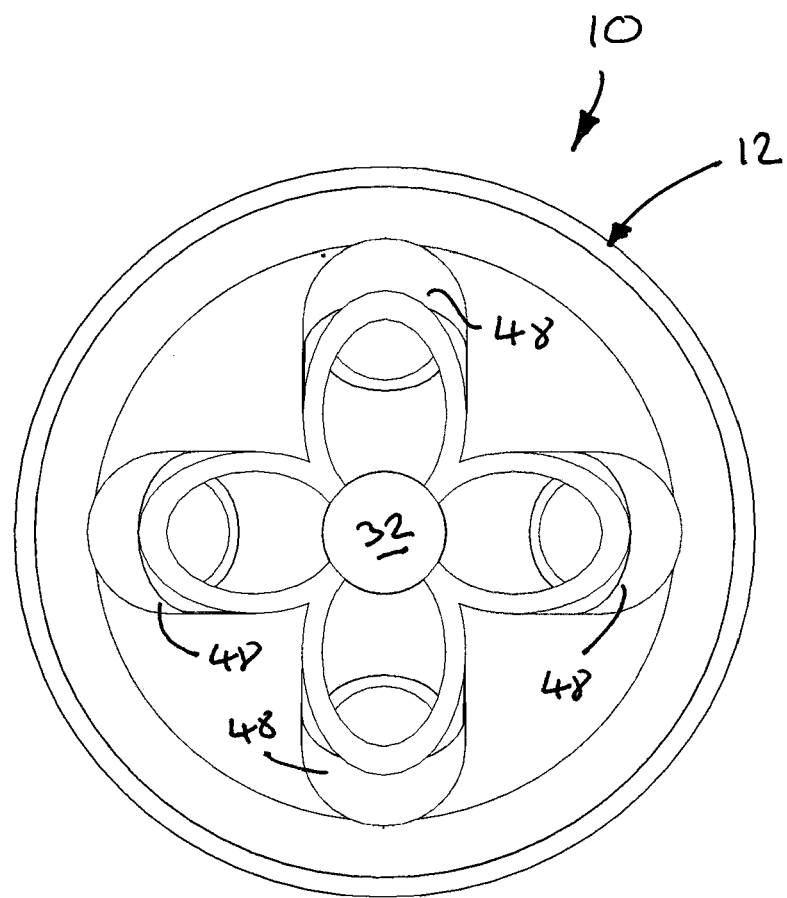
FIG. 7 shows the transverse cross-sectional view of the construct as indicated by line B-B of FIG. 4.
Figure 8:
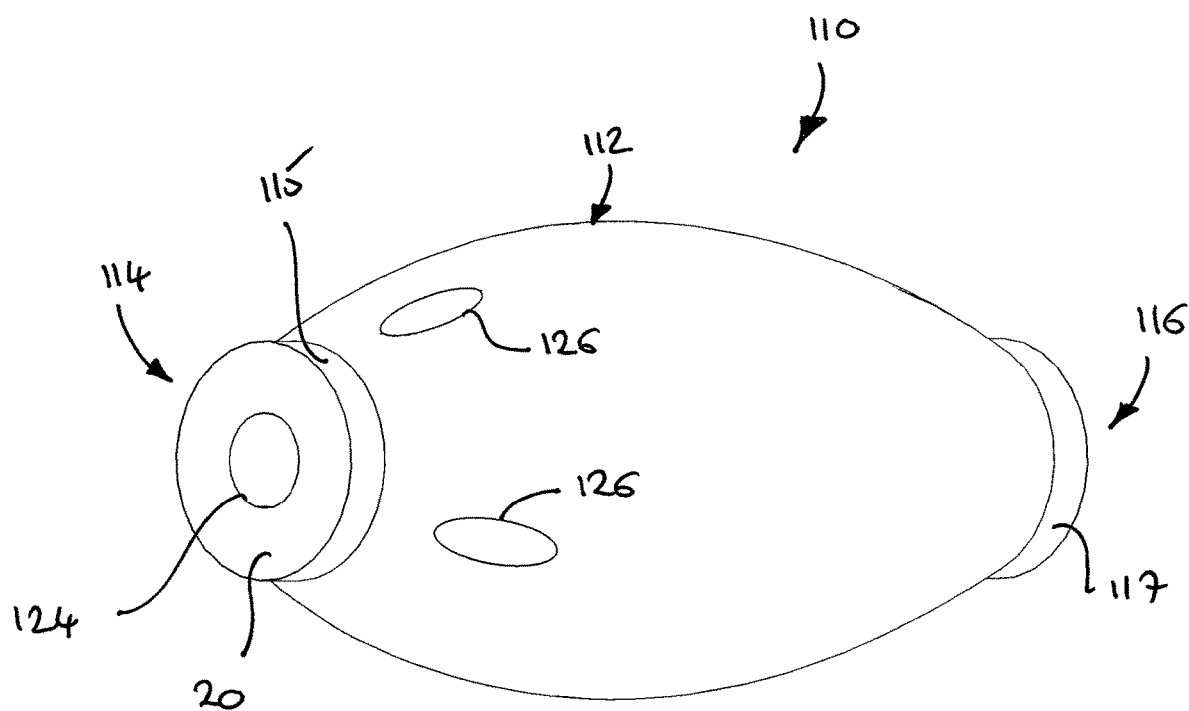
FIG. 8 shows a perspective view of a lymph node replacement construct according to a second embodiment of the present invention.
Figure 9:
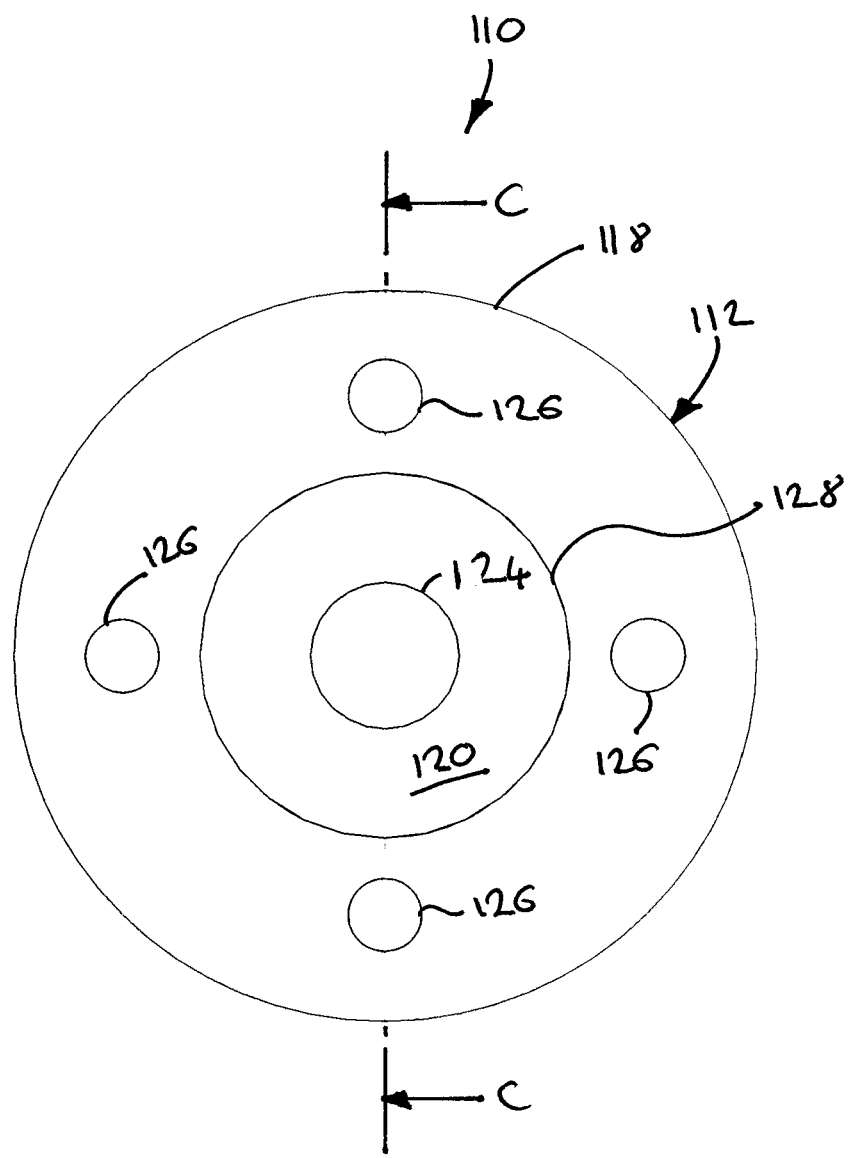
FIG. 9 shows an end view of the inlet end of the construct of FIG. 8.
Figure 10:
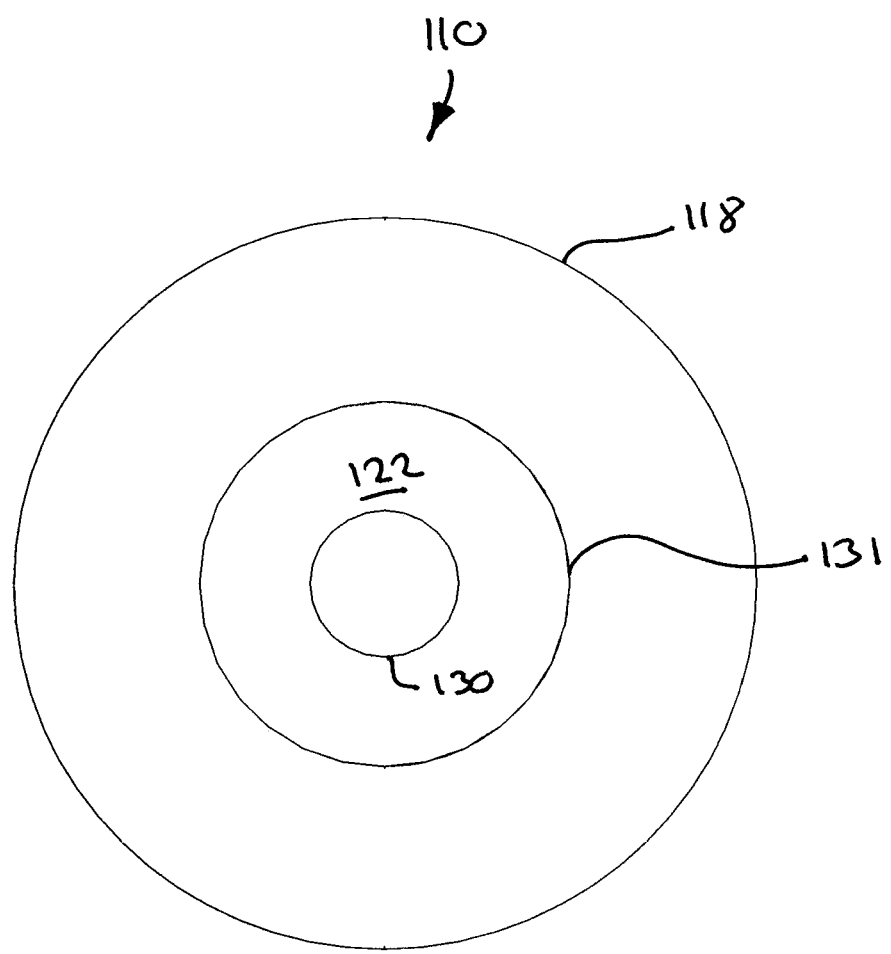
FIG. 10 shows an end view of the outlet end of the construct of FIG. 8.
Figure 11:
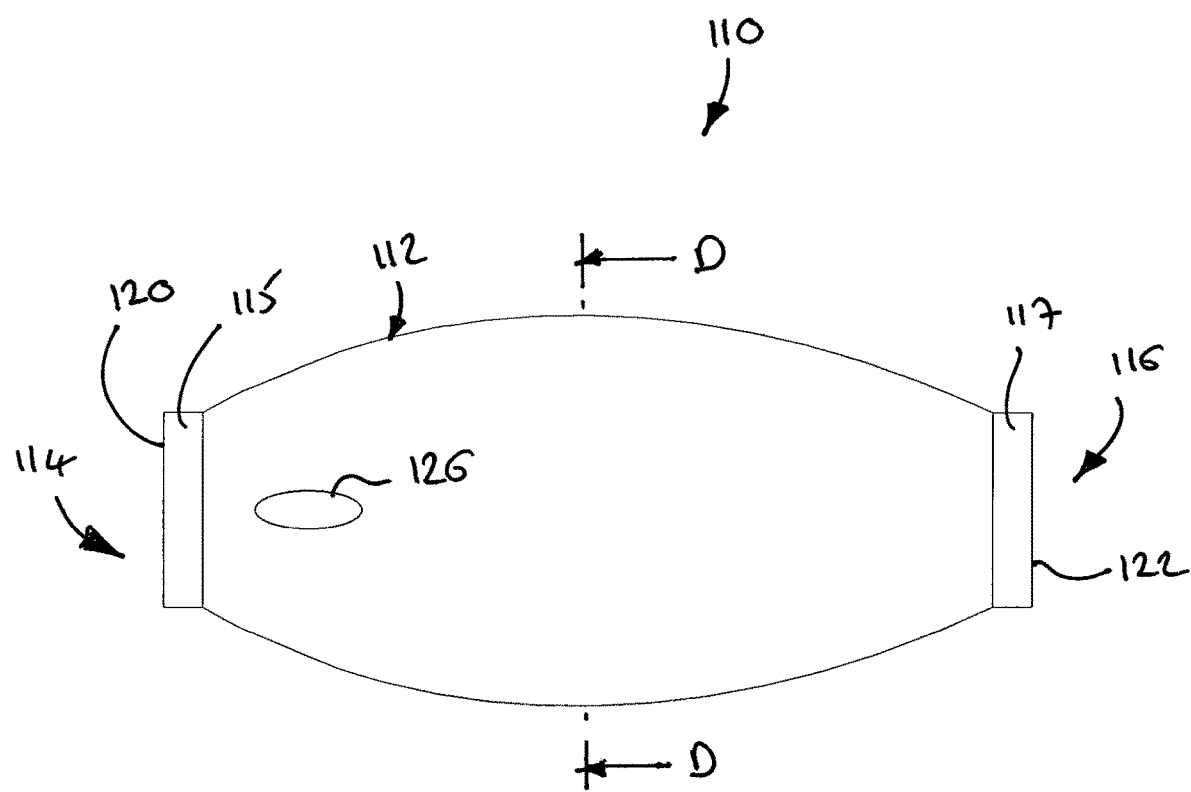
FIG. 11 shows a side view of the construct of FIG. 8.
Figure 12:
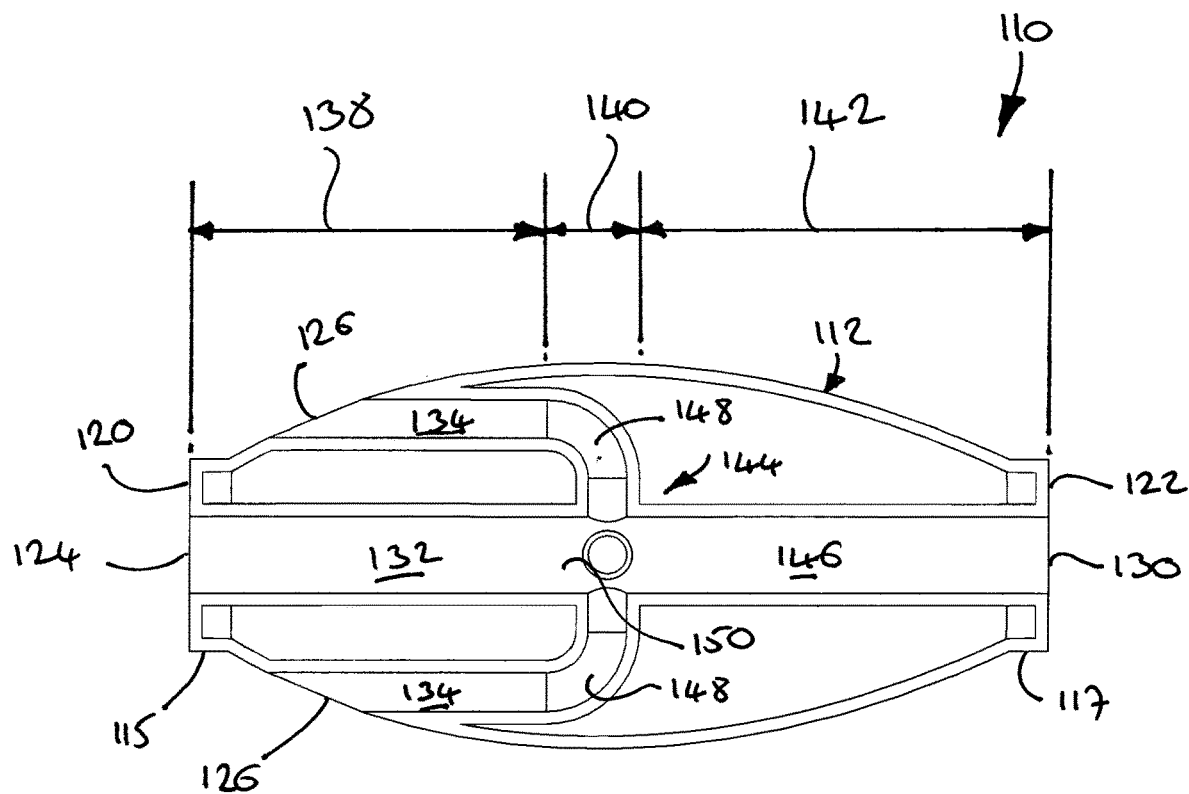
FIG. 12 shows the longitudinal cross-sectional view of the construct as indicated by line C-C of FIG. 9.
Figure 13:
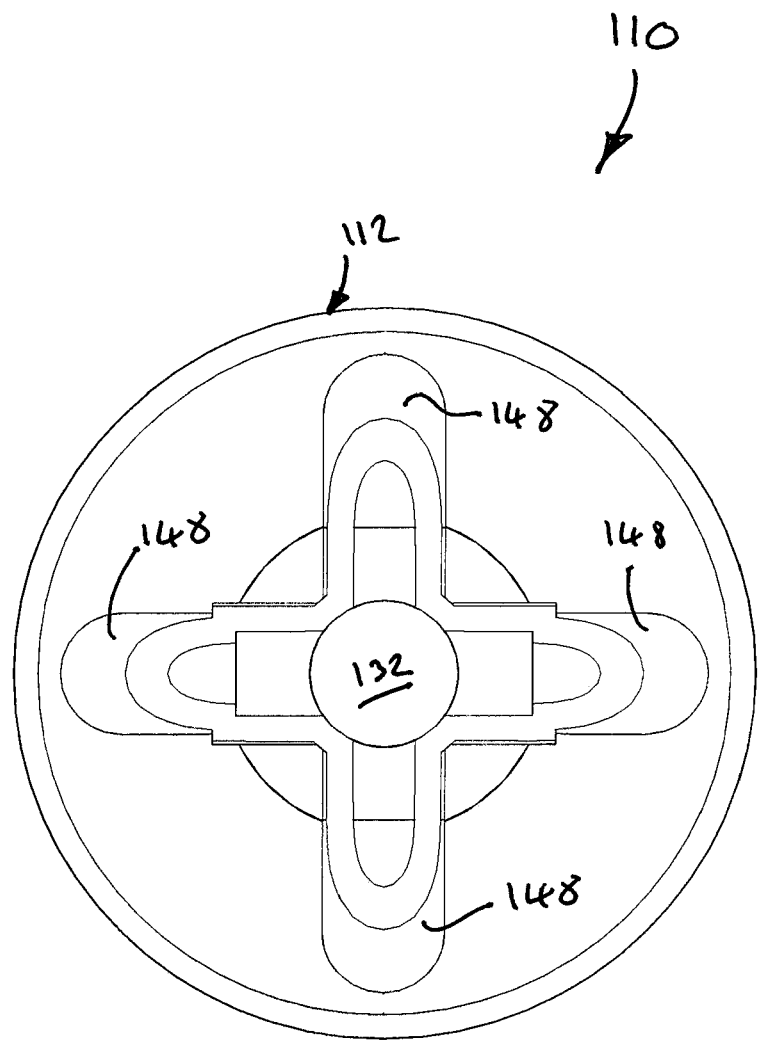
FIG. 13 shows the transverse cross-sectional view of the construct as indicated by line D-D of FIG. 11.

Turning now to cross-sectional views shown in FIGS. 5 and 6, the internal structure of the construct 10 is illustrated. In broad overview, each inlet aperture 24,26 is in fluid communication with a respective inlet conduit 32,34. The inlet conduits 32,34 converge into a common outlet conduit 36 which, in turn, is in fluid communication with the outlet aperture 30. With reference to FIG. 5, the internal structure of the construct 10 can be divided into an inlet portion 38, a convergent portion 40 and an outlet portion 42. As can be readily appreciated from FIG. 5 at least, the inlet portion, provides a plurality of parallel flow paths, which converge to a lesser number of flow paths, and preferably a single flow path, within the body 12.

In the embodiment shown, the construct 10 is illustrated with an internal space disposed between the internal structure and the body 12 and end faces 22,24. Such a space may result from the method by which the construct 10 is fabricated and may be used to retain biologically beneficial substances. Such substances are described in greater detail below. In an alternative embodiment, the space may not be provided, or may not be possible to realise due to the method of manufacture of the construct 10.

Looking firstly at the inlet portion 38, it will be noted that this comprises the five inlet conduits 32,34 arranged in substantially parallel relation to one another. It will thus be appreciated that the inlet conduits 32,34 are of substantially equal length. In the embodiment shown the inlet conduits 32,34 are all of approximately equal diameter to one another. Each conduit 32,34 is further of substantially constant diameter along its length. The inlet conduits 32,34 thus present a plurality of concurrent flow paths for lymph which extend from the inlet apertures 24,26 and through the inlet portion 38 of internal structure of the construct 10 to the convergent portion 40.

It will be appreciated that other arrangements and configurations for the inlet conduits 32, 34 may be provided. For example, the diameters of the inlet conduits 32,34 need not be all equal to one another. For example, the central inlet conduit 32 may have a greater or lesser diameter than the satellite inlet conduits 34. Alternatively, or additionally, the inlet conduits 32,34 need not be of a constant diameter along their entire length. For example, one or more of the inlet conduits 32,34 may increase and/or decrease in diameter along their length. Such variations in diameter could be utilised to provide the aforementioned flow retention spaces where lymph may be exposed to biological macromolecules and cells residing within the construct.

The inlet conduits 32,34 also need not be arranged in substantially parallel relation to one another within the inlet portion 38 of the construct 10. Instead of being aligned with respective parallel axes, the inlet conduits 32,34 may instead be aligned along convergent axes. Alternatively, inlet conduits 32, 34 may be curved, twisted or otherwise non-linear over the whole or part of their length.

Turning now to the convergent portion 40 of the internal structure of the construct 10 this, as its name suggests, is configured to effect combination of the inlet conduits 32, 34. In the embodiment shown, the convergent portion 40 takes the form of a five-into-one manifold 44. The manifold 44 is formed from extensions of the inlet conduits 32,34. More specifically, the manifold 44 is formed from inclined and convergent extensions 48 of the satellite inlet conduits 34 and a linear extension 50 of the central inlet conduit 32. The extensions 48,50 are of equal diameter to their respective inlet conduit 32,34.

The use of a five-into-one manifold 44 is described by way of example only and it will be appreciated that there exist other configurations for the internal structure of the construct 10 that achieve the same result of combining the inlet conduits 32,34. For example, the inlet conduits 32,34 may combine in a more progressive manner. In such a configuration pairs of satellite inlet conduits 34 may first combine before then combining with the central inlet conduit 32 in a three-into-one manifold. In yet another alternative embodiment, the inlet conduits 32,34 may be connected individually and separately to an accumulation chamber provided within the construct 10, the accumulation chamber itself being connected to the outlet aperture 30 of the construct.

Referring now to the outlet portion 42 of the internal structure of the construct 10, this comprises a single outlet conduit 46 which extends from the manifold 44 to the outlet aperture 30. In the embodiment shown, the outlet conduit 46 is aligned along a common axis with central inlet conduit 32 and further has a constant diameter along its length which is substantially equal to the diameter of the central inlet conduit 32. In a similar manner to the inlet conduits 32,34 described above, the outlet conduit 46 may take alternate forms and configurations. For example, the diameter of the outlet conduit 46 may vary along its length and need not extend in a straight line from the manifold 44 to the outlet aperture 30.

The construct 10 is formed from a biocompatible material 10. In one embodiment, the construct may be formed from a compliant biocompatible material, and more specifically a compliant polymer biocompatible material. Suitable polymer materials include, for example, polypropylene, polygylcolic acid, polycaprilactone and poly L lactic acid. In an alternative embodiment, compliance of the construct 10 may not be necessary and thus the construct 10 may be formed from a rigid biocompatible material. Such a rigid biocompatible material may include, for example, metals, ceramics and more rigid formulations of the aforementioned polymer biocompatible materials. The material from which the construct 10 is formed may be either bio-degradable or non-biodegradable.

The construct 10 may be formed by one or more of a number of different manufacturing operations including, for example, 3D printing, electrostatic or biological self-assembly, electrospinning and mechanical machining. It will be appreciated by the skilled addressee that the desired configuration of the construct and the material chosen for its manufacture will have a bearing on the manufacturing operation or operations required.

Biologically beneficial substances that encourage lymphatic vessel connection and ingrowth (such as lymphangiogenic vascular endothelial growth factor or VEGF-C) may optionally be included in the construct 10, either at the ends 14,16 or throughout the whole body 12 of the construct 10. The construct 10 may also contain substances such as heparin to help prevent the formation of thrombi or other fibrous materials, which could block the conduits 32,34,46. Other substances that minimise the body's natural reactions to implanted materials may be included in the construct 10 as well, with the goal of maintaining open passageways, preventing fibrous encapsulation and such like.

In use, the construct 10 functions in a manner similar to a lymph node by receiving and combining lymph from afferent lymph vessels connected to or adjacent the inlets 24,26 and delivering the combined lymph to an efferent lymph vessel connected to or adjacent the outlet 30. More specifically, lymph received at the inlets 24,26 of the construct 10 passes to the inlet conduits 32,34. The use of both multiple inlets 24,26 and corresponding multiple inlet conduits 32, 34 presents less resistance to the flow of lymph into the construct 10 than a single inlet. Lymph which has passed to the inlet conduits 32,34 is conveyed to the manifold 44 whereupon the discrete lymph flows are combined. Flow through the internal structure of the construct 10 is driven by the pressure generated in the afferent lymph vessel or vessels upstream of the construct 10, in use. The fluid pressure generated by the vessel or vessels is typically in the region of a few cm H20. Thus the importance of reducing as far as is practicable the resistance to flow into and through the construct 10 can be appreciated. The combined flow of lymph then passes to the outlet conduit 46 and exits the construct 10 via the outlet 30.

Optionally, the internal structure of the construct 10 may be provided with valves in order to limit the backflow of lymph in the direction from the outlet 30 to the inlets 24,26. Reference is now made to the cross-sectional view of the construct 10 shown in FIG. 6. The inlet conduits 32,34 and outlet conduit 46 are each provided with unidirectional valves 52,54. In the embodiment shown the inlet conduits 32,34 are each provided with a bi-leaflet type valve 52, while the outlet conduit 46 is provided with a mono-leaflet type valve 52. The valves 52,54, in use, prevent backflow while presenting minimal resistance to forward flow. The presence of bi-leaflet type valves 52 in the inlet conduits 32,34 and a mono-leaflet type valve 54 in the outlet conduit 54 is provided by way of example only, and it will be appreciated that other valve combinations are possible. For example, a unidirectional valve structure having no moving parts. An example of such a valve structure is described in U.S. Pat. No. 1,329,559.

In the embodiment shown, the inlet conduit valves 52 are aligned at a common axial position along the length of the inlet conduits 32,34. It will be appreciated that other axial positions are possible, for example the inlet conduit valves 52 may be staggered relative to one another along the length of the inlet conduits 32,34.

In use, the valves 52,54 are opened by the fluid pressure of lymph flowing through the construct 10 from the inlets 24,26 to the outlet 30. Opening of the valves 52,54 may also be achieved by manipulation, for example massage of the region in which the construct 10 is implanted.

Referring now to FIGS. 8 to 13 there is shown an alternative embodiment of a lymph node replacement construct generally designated 110. Features common to the construct 10 described with reference to FIGS. 1 to 7 are identified with like reference numerals prefixed with "1".

The construct 110 of FIGS. 8 to 13 differs from the construct 10 of FIGS. 1 to 7 as follows. The end faces of 114,116 of the construct 110 are provided upon cylindrical extensions 115,117 of the barrel shaped body 12. The central inlet aperture 124 is, as before, provided in the inlet side end face 120 of the construct 110, while the satellite inlet apertures 126 are now provided through the body 12 of the construct 110. The inlet and outlet conduits 132,146 are each of substantially equal and constant diameter along their respective lengths, while the satellite inlet conduits 134 are of a smaller diameter than the inlet and outlet conduits 132,146.

The construct 110 operates in the same manner as described above with reference to the construct 10 described in connection with FIGS. 1 to 7 by receiving and combining lymph from afferent lymph vessels connected to or adjacent the inlets 124,126 and delivering the combined lymph to an efferent lymph vessel connected to or adjacent the outlet 130. More specifically, lymph received at the inlets 124,126 of the construct 110 passes to the inlet conduits 132,134. The use of both multiple inlets 124,126 and corresponding multiple inlet conduits 132, 134 presents less resistance to the flow of lymph into the construct 110 than a single inlet. Lymph which has passed to the inlet conduits 132,134 is conveyed to the manifold 144 whereupon the discrete lymph flows are combined. The combined flow of lymph then passes to the outlet conduit 146 and exits the construct 110 via the outlet 130.

While the embodiments of the invention described above both show lymph node replacement constructs with five inlet apertures and a single outlet aperture, it will be appreciated that greater than five inlet apertures may be provided, and greater than one outlet may be provided, with the limitation that the number of outlets is less than the number of inlets. It will further be appreciated that an important feature of the invention resides in the construct having a lesser number of outlets than inlets such that lymph flow is combined within the construct. It will further be appreciated that a lymph node replacement construct in accordance with the present invention may have fewer than five inlets. In keeping with the principles of the invention, a construct may have as few as two inlets in fluid communication with a single outlet via the internal structure of the construct.

Figure 14:
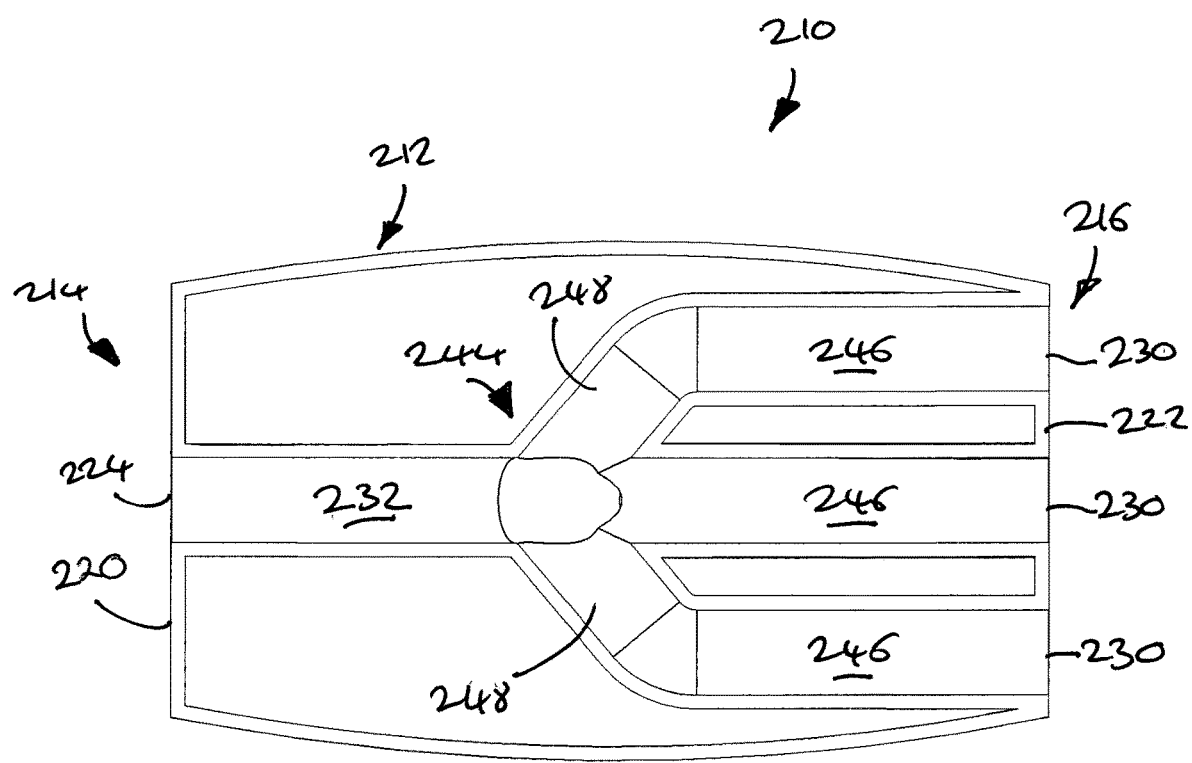
FIG. 14 shows a longitudinal cross-sectional view of a lymph node replacement construct according to a third embodiment of the present invention.

FIG. 14 shows a longitudinal cross-sectional view of a further alternative embodiment of a lymph node replace construct generally designated 210. Features common to the construct 10 described with reference to FIGS. 1 to 7 are identified with like reference numerals prefixed with "2". The construct 210 has the same configuration as the construct 10 of FIGS. 1 to 7 but with its direction reversed. As such, the construct 210 has a single inlet aperture 224 and multiple outlet apertures 230, and the manifold 244 acts to split the lymph flow entering the construct 210 as opposed to combining multiple flows. Such a configuration may be beneficial in instances where the construct 210 is required to interface with a single afferent vessel and multiple efferent vessels. It will be appreciated by the skilled addressee that different arrangements of the construct 210 are possible where the number of outlets is greater than the number of inlets, and that flow splitting occurs within the construct 210. As can be readily appreciated from FIG. 14 at least, the inlet portion provides at least one flow path in the inlet portion, diverging to a greater numbering plurality of parallel flow paths in the outlet portion, within the body 12.

Figure 15:
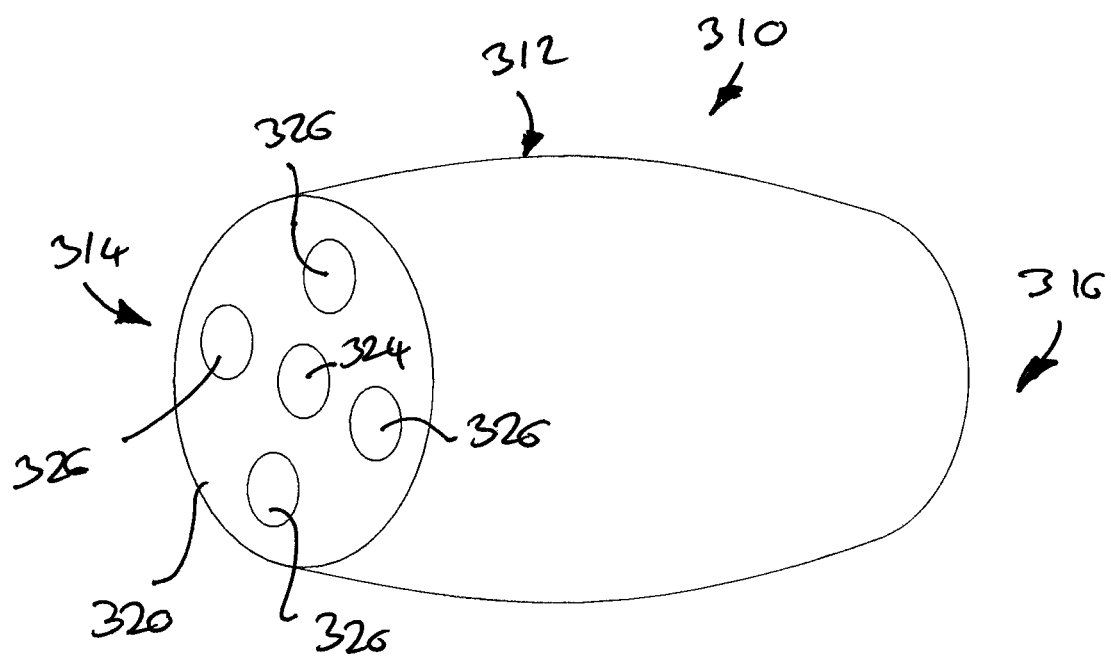
FIG. 15 shows a perspective view of a lymph node replacement construct according to a fourth embodiment of the present invention.
Figure 16:
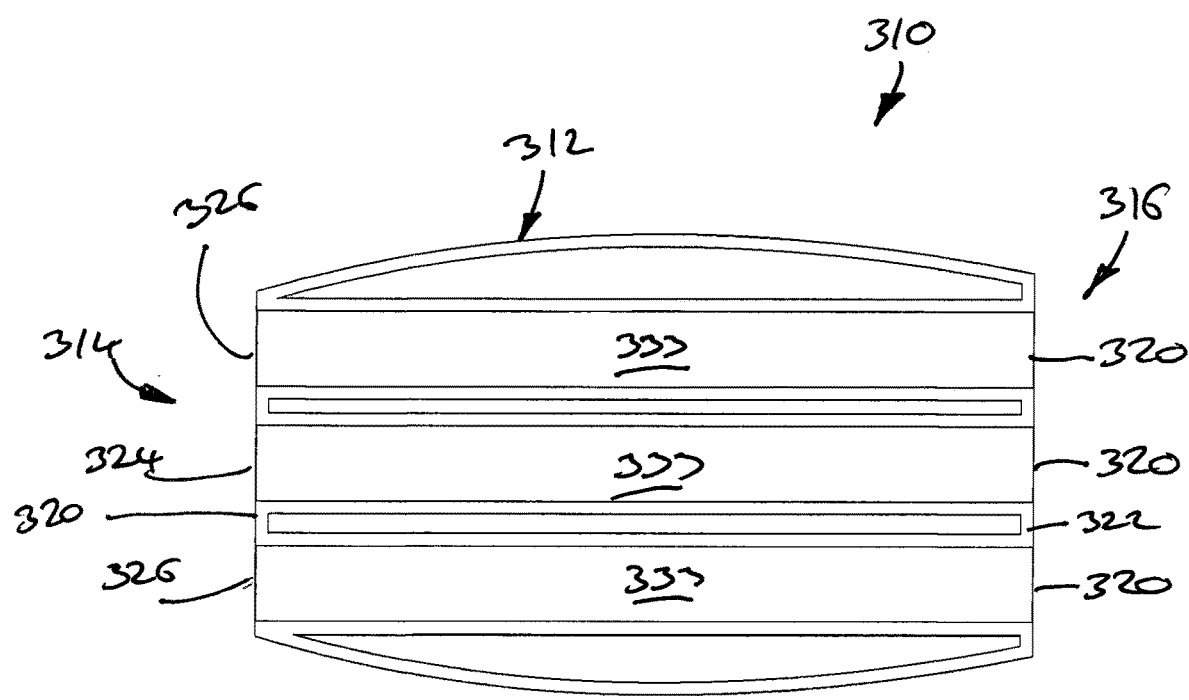
FIG. 16 shows a longitudinal cross-sectional view of the construct of FIG. 15.

FIGS. 15 and 16 show perspective and longitudinal cross-sectional views of a further alternative embodiment of a lymph node replace construct generally designated 310. Features common to the construct 10 described with reference to FIGS. 1 to 7 are identified with like reference numerals prefixed with "3". The construct 310 is provided with a plurality of inlet apertures 324,326 and a corresponding plurality of outlet apertures 330. The internal structure of the construct 310 differs in that there is no manifold. Instead, each inlet aperture is connected to a single outlet aperture via a separate conduit 333 extending through the construct 310. As can be readily appreciated from FIGS. 15 and 16, the conduits 333 are parallel flow paths extending in parallel through and within the body 12.

The constructs 210,310 described with reference to FIGS. 14 to 16 may include features described with reference to the previously described embodiments such as unidirectional valves and biologically beneficial substances.

What is claimed is:

1. An implant comprising:
   a body having one or more inlets on an exterior of the body and having one or more outlets on the exterior of the body, wherein the one or more inlets are each spaced from the one or more outlets in an axial dimension;
   the body further having:
   an internal structure defining a fluid communication path through the body, from the inlet or inlets, to the outlet or outlets, the internal structure being enclosed within the body, which surrounds the internal structure;
   wherein the implant is configured to function as a lymph node replacement construct by receiving lymph from one or more afferent lymph vessels when connected to or adjacent the inlet or inlets, and delivering the lymph to one or more efferent lymph vessels when connected to or adjacent the outlet or outlets;
   wherein the fluid communication path comprises a plurality of parallel or substantially parallel flow paths extending substantially in the axial dimension, in side-by-side relation to one another, and through and within at least a part of the body, the internal structure configured such that lymph received by the body at the inlet or inlets is conveyed through the parallel or substantially parallel flow paths within the body by proceeding at least substantially in the axial dimension, before passing to the outlet or outlets;
   wherein the body comprises a first body section, a second body section, and a third body section, wherein the third body section is disposed between the first body section and the second body section proceeding along the axial dimension;
   wherein the first body section comprises a plurality of inlets and a separate first conduit for each inlet such that there are a plurality of first conduits and with each inlet of the plurality of inlets then having a dedicated first conduit, wherein the plurality of first conduits provide the parallel or substantially parallel flow paths of the fluid communication path such that lymph proceeds at least substantially in the axial dimension within the plurality of the parallel or substantially parallel flow paths;
   wherein the third body section comprises a manifold that is disposed within the interior of the body, wherein each first conduit of the first body section extends from its corresponding inlet to the manifold of the third body section;
   wherein the second body section comprises a single outlet disposed on the exterior of the body, wherein the second body section further comprises a single conduit in the form of a second conduit that is disposed within the interior of the body and that extends from the manifold of the third body section to the single outlet of the second body section;
   wherein the fluid communication path comprises the plurality of first conduits, the manifold, and the second conduit;
   wherein the implant is configured: a) for each of the plurality inlets of the first body section to be connected or disposed adjacent to a corresponding lymph vessel of a first type; and b) for the single outlet of the second body section to be connected or disposed adjacent to a single lymph vessel of a second type.

2. An implant according to claim 1, wherein the plural parallel flow paths are encapsulated within a common enclosure defined by the body.

3. An implant according to claim 1, wherein the body comprises an outer surface extending around the plural parallel flow paths, so that the flow paths are laterally contained within the outer surface.

4. An implant according to claim 1, wherein the internal structure of the body comprises an inlet portion, a convergent portion and an outlet portion such that lymph received by the body at each inlet is conveyed through the inlet portion of the internal structure to the convergent portion, whereupon the lymph is combined before passing to the single outlet, wherein the first body section comprises the inlet portion, wherein the third body section comprises the convergent portion, and wherein the second body section comprises the outlet portion.

5. An implant as claimed in claim 1 wherein the internal structure of the body includes a unidirectional valve arranged to prevent the backflow of lymph in the direction from the single outlet to the plurality of inlets.

6. An implant as claimed in claim 1 wherein each first conduit includes a unidirectional valve arranged to prevent the backflow of lymph in the direction from the single outlet to the plurality of inlets.

7. An implant as claimed in claim 1 wherein the second conduit includes a unidirectional valve arranged to prevent the backflow of lymph in the direction from the single outlet to the plurality of inlets.

8. An implant as claimed in claim 5, further comprising first and second unidirectional valves, the first unidirectional valve arranged between the second unidirectional valve and the plurality of inlets, or the single outlet, such that external manipulation of the construct opens the valves to assist in the movement of lymph in the construct.

9. An implant according to claim 8, configured such that external manipulation of the construct pumps lymph through the device via the unidirectional valves.

10. An implant according to claim 6, wherein each unidirectional valve is a mono-leaflet type valve.

11. An implant as claimed in claim 6, wherein each unidirectional valve is a bi-leaflet type valve.

12. An implant as claimed in claim 1 wherein the construct is fabricated from a compliant, resilient material.

13. An implant as claimed in claim 1 wherein the construct includes one or more biologically active substances disposed within the internal structure of the body.

14. An implant as claimed in claim 13 wherein the one or more biologically active substances comprise growth factors or other substances that encourage lymphatic vessel connection and ingrowth.

15. An implant comprising:
   a body having one or more inlets on an exterior of the body and having one or more outlets on the exterior of the body, wherein the one or more inlets are each spaced from the one or more outlets in an axial dimension;
   the body further having:
   an internal structure defining a fluid communication path through the body, from the inlet or inlets, to the outlet or outlets, the internal structure being enclosed within the body, which surrounds the internal structure;

wherein the implant is configured to function as a lymph node replacement construct by receiving lymph from one or more afferent lymph vessels when connected to or adjacent the inlet or inlets, and delivering the lymph to one or more efferent lymph vessels when connected to or adjacent the outlet or outlets, wherein the fluid communication path comprises a plurality of parallel or substantially parallel flow paths extending substantially in the axial dimension, in side-by-side relation to one another, and through and within at least a part of the body, the internal structure configured such that lymph received by the body at the inlet or inlets is conveyed through the parallel or substantially parallel flow paths within the body by proceeding at least substantially in the axial dimension, before passing to the outlet or outlets, wherein the internal structure of the body comprises an inlet portion, a convergent portion and an outlet portion such that lymph received by the body at each inlet is conveyed through the inlet portion of the internal structure to the convergent portion, whereupon the lymph is combined before passing to the outlet or outlets.

16. An implant as claimed in claim 15 wherein the inlet portion of the internal structure of the body includes a corresponding plurality of inlet conduits extending from a corresponding plurality of inlets to the convergent portion.

17. An implant as claimed in claim 16 wherein the convergent portion of the internal structure of the body comprises a manifold extending from the inlet conduits to the outlet portion of the internal structure of the body.

18. An implant as claimed in claim 17 wherein the outlet portion of the internal structure of the body comprises one or more outlet conduits extending from the manifold to the outlet or outlets of the body.

19. An implant as claimed in claim 16 wherein one or more of the inlet conduits includes a unidirectional valve arranged to prevent the backflow of lymph in the direction from the outlet or outlets to the inlets.

20. An implant as claimed in claim 18 wherein each outlet conduit includes a unidirectional valve arranged to prevent the backflow of lymph in the direction from the outlet or outlets to the inlet or inlets.

* * * * *